(12) United States Patent
Gabi et al.

(10) Patent No.: US 9,162,778 B2
(45) Date of Patent: Oct. 20, 2015

(54) METHOD FOR SPATIALLY MANIPULATING A MICROSCOPIC OBJECT AND DEVICE FOR CONDUCTING SAID METHOD

(75) Inventors: Michael Gabi, Zürich (CH); Janos Voeroes, Zürich (CH); Stefan Pablo Doerig, Zürich (CH); Pascal Behr, Zürich (CH); Philipp Stiefel, Zürich (CH); Thomaso Zambelli, Zürich (CH); Julia Vorholt-Zambelli, Zürich (CH)

(73) Assignee: ETH Zürich, Zürich (CH)

( * ) Notice: Subject to any disclaimer, the term of this patent is extended or adjusted under 35 U.S.C. 154(b) by 292 days.

(21) Appl. No.: 13/580,936

(22) PCT Filed: Feb. 7, 2011

(86) PCT No.: PCT/CH2011/000020
§ 371 (c)(1),
(2), (4) Date: Nov. 13, 2012

(87) PCT Pub. No.: WO2011/103691
PCT Pub. Date: Sep. 1, 2011

(65) Prior Publication Data
US 2013/0105034 A1 May 2, 2013

(30) Foreign Application Priority Data
Feb. 26, 2010 (CH) ....................... 249/10

(51) Int. Cl.
*B01L 9/00* (2006.01)
*G01N 35/00* (2006.01)
(Continued)

(52) U.S. Cl.
CPC . *B65B 1/04* (2013.01); *B82Y 35/00* (2013.01); *C12M 33/04* (2013.01); *G01Q 60/38* (2013.01); *B82Y 5/00* (2013.01); *B82Y 30/00* (2013.01); *G01Q 80/00* (2013.01)

(58) Field of Classification Search
USPC ............................... 422/560; 436/43
See application file for complete search history.

(56) References Cited

U.S. PATENT DOCUMENTS 6,094,971 A * 8/2000 Edwards et al. ............... 73/105
6,358,749 B1 * 3/2002 Orthman ...................... 436/177
(Continued)

FOREIGN PATENT DOCUMENTS

DE 198 06 639 A1 8/1999
EP 0 307 940 A1 3/1989
(Continued)

OTHER PUBLICATIONS

Meister, Andre et al., "FluidFM: Combining Atomic Force Microscopy and Nanofluidics in a Universal Liquid Delivery System for Single Cell Applications and Beyond", Nano Letter, Jun. 2009, pp. 2501-2507, v9:6.
(Continued)

*Primary Examiner* — Jill Warden
*Assistant Examiner* — Brittany Fisher
(74) *Attorney, Agent, or Firm* — Pauley Erickson & Kottis

(57) ABSTRACT

The invention relates to a method for spatially manipulating a microscopic object including providing a cantilever (12) having a tip with an opening (19) and a microchannel (15) extending through the cantilever (12) in its longitudinal direction. A suspension means is provided for holding the cantilever (12) and spatially moving the cantilever along a predetermined spatial path. A pressurizing means is provided for applying a predetermined pressure to the microchannel (15) and the cantilever (12) is moved with its tip to the microscopic object to be spatially manipulated. At least a part of the microscopic object is picked up with said cantilever (12) by reducing the pressure within the microchannel (15) relative to the pressure outside the tip of the cantilever (12). The microscopic object is then moved along a predetermined spatial path by means of the cantilever (12).

17 Claims, 6 Drawing Sheets

(51) Int. Cl.
  *B65B 1/04*   (2006.01)
  *B82Y 35/00*  (2011.01)
  *C12M 1/26*   (2006.01)
  *G01Q 60/38*  (2010.01)
  *B82Y 5/00*       (2011.01)
  *B82Y 30/00*      (2011.01)
  *G01Q 80/00*      (2010.01)

(56) References Cited

U.S. PATENT DOCUMENTS

| | | | |
|---|---|---|---|
| 6,977,033 B2 * | 12/2005 | Becker et al. | 204/450 |
| 2006/0214330 A1 * | 9/2006 | Dumond et al. | 264/320 |
| 2007/0210677 A1 * | 9/2007 | Larson et al. | 310/338 |
| 2008/0314131 A1 | 12/2008 | Yasutake et al. | |
| 2011/0075161 A1 * | 3/2011 | Byun et al. | 358/1.8 |

FOREIGN PATENT DOCUMENTS

| | | |
|---|---|---|
| EP | 2 083 257 A1 | 1/2008 |
| EP | 1 990 626 A1 | 11/2008 |
| JP | 4-105040 | 4/1992 |
| JP | 2001-183289 | 7/2001 |
| JP | 2001-324375 | 11/2001 |
| JP | 2005-312343 | 11/2005 |
| JP | 2007-319034 | 12/2007 |
| JP | 2008-64621 | 3/2008 |
| JP | 2008-79608 | 4/2008 |
| WO | WO 2009/092495 A1 | 7/2009 |
| WO | WO 2010/012423 A1 | 2/2010 |

OTHER PUBLICATIONS

Furutani, Katsushi et al, "Application of AZARASHI (Seal) Positioning Mechanism to Micromanipulation by Vacuum Suction", Optomechatronic Technologies, Int'l Symposium on, 2009, pp. 65-70, ISBN: 978-1-4244-4209-6.

G. Binnig et al., "The atomic force microscope AFM," Phys Rev Lett, 1986, vol. 56, Issue 9, p. 930-933 (Abstract Only).

* cited by examiner

METHOD FOR SPATIALLY MANIPULATING A MICROSCOPIC OBJECT AND DEVICE FOR CONDUCTING SAID METHOD

BACKGROUND OF THE INVENTION

1. Field of the Invention

The present invention pertains to the field of manipulating microscopic objects such as bacteria, biological cells, neurons, or submicron objects such as virus or nanoparticles, or the like.

2. Discussion of Related Art

The ability to obtain information at the single-cell level is becoming of central importance for numerous biological questions and represents a major challenge. There is an increasing awareness that individual cells, although genetically identical to sister cells, show different phenotypes and expression profiles of genes (transcripts) and in consequence levels of proteins and metabolites. New innovative technologies are required to address individual cells, whereby "to address" has a broad meaning ranging from displacement, injection up to analysis. For the following the focus shall be on the controlled spatial displacement of single cells.

Several years ago A. Ashkin and co-workers pioneered the development of the optical tweezers as mean to manipulate biological objects (see for example EP 307 940). Exploiting the trapping forces due to the radiation pressure through intense and collimated lasers, they showed that one could handle viruses, bacteria, cells up to cellular organellae. Yet, it is still debated at which extent optical tweezers damage the trapped organisms.

Glass micropipettes, the oldest instrument to manipulate single organisms, are not truly apt for displacement experiments. Operated by means of micromanipulators combined with a pressure controller for the suction of the biological objects, their positioning is still followed with optical microscopy which is limited by its intrinsic resolution of the order of 1µ. Consequently, the approach toward an organism without damaging it is a hit-and-miss procedure, while if successfully sucked, it is practically impossible to safely reposition it onto another location of the substrate surface.

The atomic force microscope AFM (G. Binnig, C. F. Quate, and C. Gerber, Phys Rev Lett 56 (9), 930 (1986)) has the required force feedback in the pN range. With respect of organism manipulation, it is employed for a bright spectrum of adhesion experiments but it is not conceived for displacement experiments because organisms are stably attached to the underside of the cantilever preventing their release on another position of the substrate.

SUMMARY OF THE INVENTION

The development of the "FluidFM" (A. Meister, M. Gabi, P. Behr, P. Studer, J. Vo-ros, P. Niedermann, J. Bitterli, J. Polesel-Maris, M. Liley, H. Heinzelmann, and T. Zambelli, Nano Lett 9 (6), 2501 (2009)) combining the precise AFM force feedback with nanofluidics via an incorporated microchannel directly in the cantilever (see EP-A1-1 990 626) opens novel strategies for the spatial manipulation of biological objects. The microchannel in the cantilever ends with a submicron aperture at the apex of the pyramidal tip and on the other side with a reservoir. A channel is also machined in the AFM probeholder. By conveniently fixing the chip against the probeholder, a continuous fluidic pipeline is obtained connecting the tip aperture with a syringe or a pressure controller. Therefore, the "FluidFM" can be immersed in liquid environment while a pressure can be applied to the solution inside the channel.

The probing area of the "FluidFM" is shown in FIG. 1: The atomic force microscope (AFM) 10 of FIG. 1 comprises a probeholder 11, which is attached to a micro-manipulating mechanism of the AFM not shown. Attached to the probeholder 11 is an elongated cantilever 12, which is fabricated by means of an MEMS (Micro-Electro-Mechanical-Systems) technology. The cantilever 12 is provided with an internal microchannel 15, which extends in the longitudinal direction of the cantilever 12. The microchannel 15 is, with its outer end, in hydraulic connection with an opening 19 a pyramidal tip 13 of the cantilever 12. At the other end, the microchannel 15 connects to a supply channel 14 running through the probeholder 11 to receive a predetermined fluid pressure from an external controllable pressure source 17 via a tubing 16. FIG. 1 further shows an impedance measuring means 34, which is connected to the liquid path. This impedance measuring means 34 is not part of the well-known "FluidFM" device, but is a novel feature of the device according to the invention, which will be explained in detail below.

The "FluidFM" is used for local liquid dispensing and stimulation of single living cells under physiological conditions. The nanofluidic microchannel 15 in the cantilever 12 allows soluble molecules to be dispensed through the submicro-meter aperture or opening 19 in the AFM tip. The sensitive AFM force feedback, which is established by means of a laser beam 18, allows controlled approach of the tip to a sample for extremely local modification of surfaces in liquid environments. It also allows reliable discrimination between gentle contact with a cell membrane or its perforation. Using these two procedures, dyes have been introduced into individual living cells and even selected subcellular structures of these cells.

Now, it is a central object of the invention to establish a method for spatially manipulating a microscopic object by using device based on the principles of the "FluidFM" described above.

It is a further object of the invention to provide a device for spatially manipulating a microscopic object according to the inventive method.

The method according to the present invention comprises the steps of: providing a cantilever having a tip with an opening and a microchannel extending through the cantilever in its longitudinal direction, said microchannel being fluidly connected to the opening at the tip of the cantilever; providing suspension means for holding the cantilever and spatially moving the cantilever along a predetermined spatial path; providing pressurizing means for applying a predetermined pressure to the microchannel within the cantilever; moving the cantilever with its tip to the microscopic object to be spatially manipulated, such that the opening of the tip is adjacent to the microscopic object; picking up, with said cantilever, a part of the microscopic object or the microscopic object as a whole by reducing the pressure within the microchannel relative to the pressure outside the tip of the cantilever; and moving said part of the microscopic object or said microscopic object as a whole along a predetermined spatial path by means of the cantilever.

An embodiment of the inventive method is characterized in that, in a further step, said part of the microscopic object or said microscopic object as a whole is released from the cantilever by increasing the pressure within the microchannel relative to the pressure outside the tip of the cantilever.

According to another embodiment of the inventive method, said part of the microscopic object or said microscopic object as a whole is picked up by introducing it into the interior of the cantilever, especially into the microchannel of the cantilever.

According to another embodiment of the inventive method, said part of the microscopic object or said microscopic object as a whole is released into a recess or into an opening of a processing means for being processed.

Another embodiment of the inventive method is characterized in that a cantilever with an elongated tip of high aspect ratio extending perpendicular to the longitudinal direction of the cantilever is used to pick up one specific microscopic object from an aggregation of several microscopic objects.

Another embodiment of the inventive method is characterized in that a cantilever with a sharpened tip extending perpendicular to the longitudinal direction of the cantilever is used to tear off a part of a microscopic object.

Another embodiment of the inventive method is characterized in that the pressurizing means comprises a pressure source, which produces by means of a pump or by capillary, osmotic or electro-osmotic forces.

Another embodiment of the inventive method is characterized in that a cantilever is used, the surface of which is modified to avoid an adhesion of the microscopic object, and especially by either having hydrophilic or hydrophobic properties.

According to another embodiment of the inventive method, during picking up the a microscopic object, the corresponding deflection of the cantilever, which is due to an adhesion force acting between said microscopic object and the surface supporting said microscopic object, is used to calculate said adhesion force.

According to another embodiment of the inventive method, during picking up, the impedance through the opening of the cantilever is measured in order to characterize the tightness of the microscopic object closing the opening.

According to another embodiment of the inventive method, the impedance through the microchannel of the cantilever is measured in order to determine the number and/or mass of microscopic objects collected in said microchannel after being picked up by said cantilever.

Just another embodiment of the inventive method is characterized in that the cantilever is sensed by means of a laser beam in order to determine the number and/or mass of microscopic objects collected in said microchannel after being picked up by said cantilever. Instead of a laser beam, a tuning fork or piezo resistive element, or another suitable sensing means may be used.

The device according to the invention comprises: a cantilever having a tip with an opening and a microchannel extending through the cantilever in its longitudinal direction, said microchannel being fluidly connected to the opening at the tip of the cantilever; suspension means for holding the cantilever and spatially moving the cantilever along a predetermined spatial path; and pressurizing means for applying a predetermined pressure to the microchannel within the cantilever; whereby said pressurizing means is configured to generate a pressure within the microchannel which is lower than the pressure outside the tip of the cantilever, and whereby a hydraulic impedance measuring means is provided for measuring the hydraulic impedance within the cantilever.

According to an embodiment of the inventive device, the opening of the cantilever is flush with the outer surface of the cantilever.

According to another embodiment of the inventive device, the cantilever has an elongated, especially cylindrical, tip of high aspect ratio extending perpendicular to the longitudinal direction of the cantilever.

According to another embodiment of the inventive device, the cantilever has a sharpened tip extending perpendicular to the longitudinal direction of the cantilever.

According to another embodiment of the inventive device, the cantilever has a pyramidal tip extending perpendicular to the longitudinal direction of the cantilever. Other geometric shapes of the tip are possible but perhaps not easy to integrate into the cantilever.

According to just another embodiment of the inventive device, the microchannel of the cantilever is configured to receive one or more of said microscopic objects.

BRIEF DESCRIPTION OF THE DRAWINGS

The invention will now be explained in detail with respect to the drawings.

DETAILED DESCRIPTION OF THE INVENTION

So far, only pulled glass micropipettes or optical tweezers can be used to displace microscopic objects with the disadvantage of not having control over the applied force to the object. Another kind of sample manipulating apparatus, which is based on an atomic force microscope (AFM), and which uses a mechanical tweezer, is disclosed in the document US-A1 2008/0314131.

The adhesion force of cells is measured nowadays by a laborious process. Cells or bacteria are grown on a cantilever bar for about 30 min and then brought in contact with a surface. There the cell has to adhere for another 30 min before the cantilever can be retracted and the adhesion force can be measured. Or vice versa, the cell is attached first to the surface. This is also a limitation of this method since the attachment of the cell to the cantilever may induce cellular changes or surface property changes, since additional adhesive molecules have to be introduced or the cells undergo already other biological processes changing the cell adhesive properties.

Figure 1:
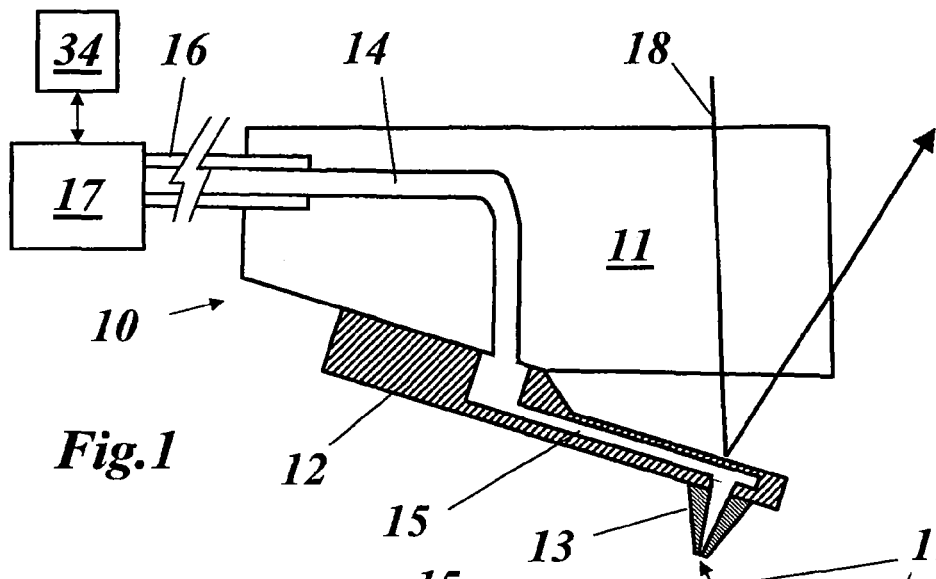
FIG. 1 shows the probing area of a device according to an embodiment of the invention, which is based on the "FluidFM" design and comprises means for measuring the hydraulic impedance within the channelled cantilever.
Figure 2:
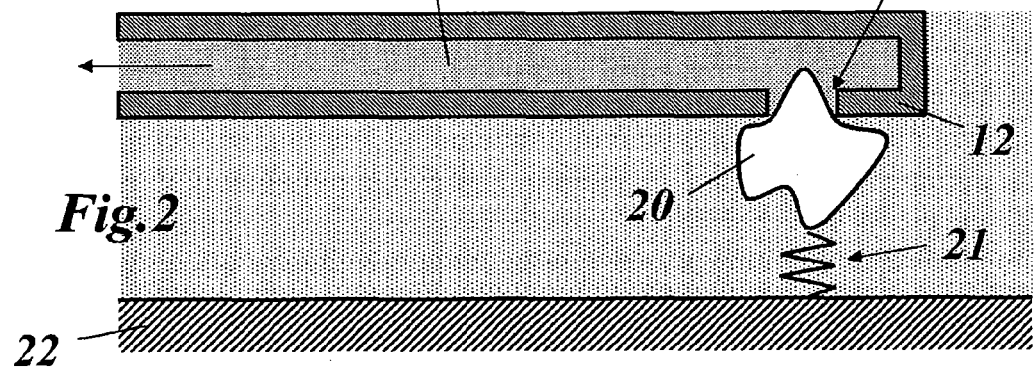
FIG. 2 shows a magnification of the hollow cantilever picking up a microscopic object by applying a negative pressure inside the cantilever in accordance with the method according to the invention.

With the present invention this whole measurement can be performed in less than a minute. As shown in FIG. 2, the hollow cantilever 12 approaches with its tip opening 19 a microscopic object or cell 20 lying on a surface 22, under force control without risking cellular damage. By applying a negative pressure (<1 bar) with respect to the fluid environment of the cantilever 12 the object or cell 20 is partly sucked into the opening 19 and is kept there, like with a suction cup. The quality of the sealing between the object 20 and the inner rim of the opening 19 can be controlled and monitored by measuring simultaneously the impedance through the cantilever tip opening 19 with the impedance measuring means 34 (see FIG. 1). To do this electrically, electrodes 35 may be placed at suitable positions in and outside the cantilever 12 (see FIG. 3).

Figure 3:
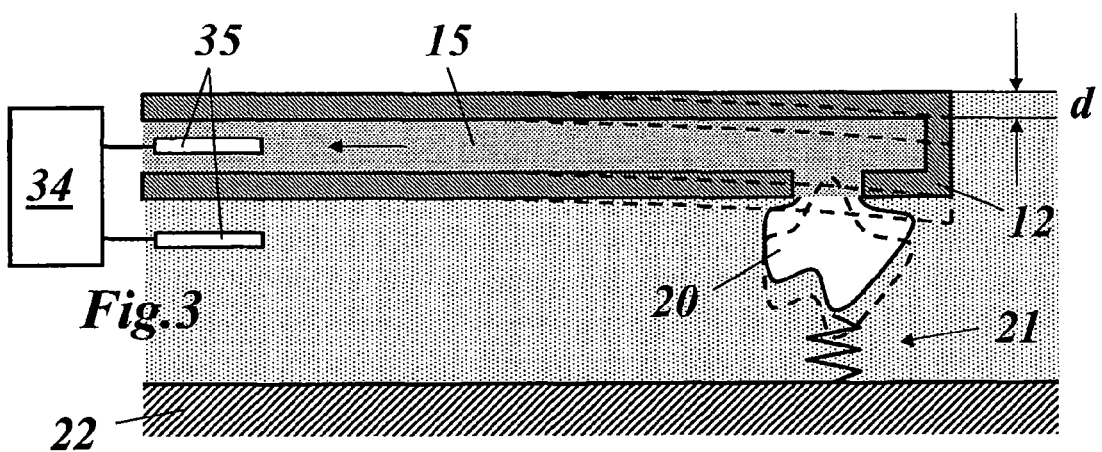
FIG. 3 shows the cantilever picking up a microscopic object, thereby measuring the adhesive force by means of the deflection of the cantilever in accordance with an embodiment of the inventive method.

The object or cell 20 now can be simply pulled away from the surface by retracting the cantilever 12 and measuring the adhesion force 21 (symbolized by a spring) at the same time (FIG. 3). The adhesion force 21 is measured by the deflection d of the cantilever 12.

The object or cell 20 can then be unloaded from the tip by either releasing the negative pressure or apply a small overpressure, so that the cantilever 12 can be reused immediately for the next adhesion force measurement. This allows fast and fully automated serial measurement of adhesion forces. Moreover the system can simply be used to spatially manipulate cells or other microscopic objects 20.

Figure 11:
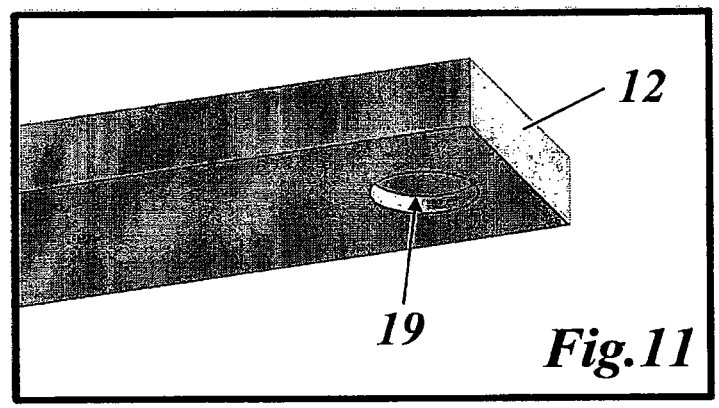
FIG. 11 shows, in a perspective view, a cantilever with a flat/blunt tip, according to an embodiment of the invention.
Figure 12:
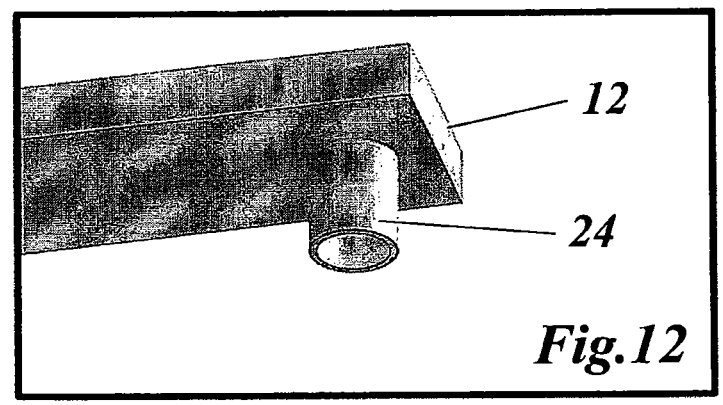
FIG. 12 shows, in a perspective view, a cantilever with a cylindrical tip with a high aspect ratio, according to another embodiment of the invention.
Figure 13:
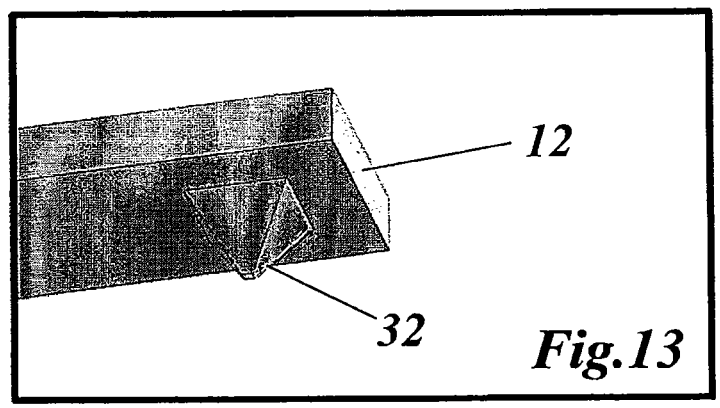
FIG. 13 shows, in a perspective view, a cantilever with a pyramidal tip, according to another embodiment of the invention.

The opening 19 of the hollow cantilever 12 can be only a simple hole (flat/blunt tip, see FIG. 11), or at the end of cylindrical or pyramidal tip structure (24 in FIGS. 12 and 32 in FIG. 13). The applied force is detected by measuring the bending of the cantilever with a deflected laser beam (18 in FIG. 1), or a tuning fork or piezoresistive material attached to the cantilever 12.

Figure 4:
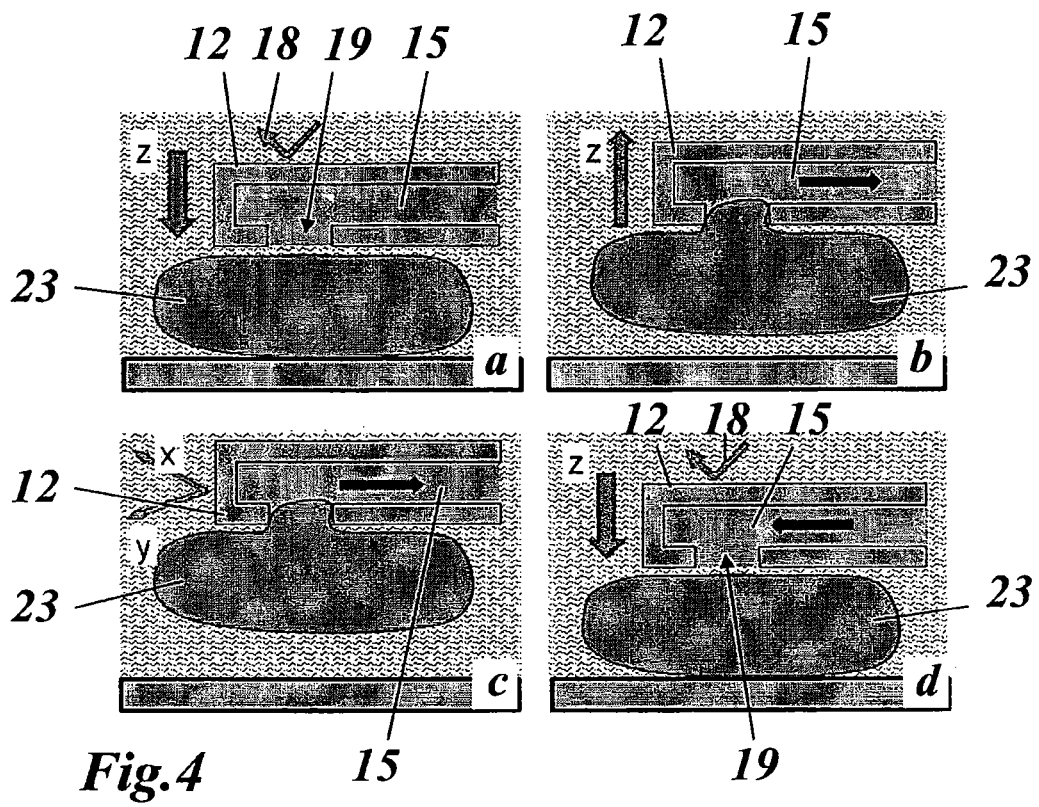
FIG. 4 shows various steps of the manipulation procedure according to the invention, whereby (a) relates to a force-controlled approach of the cantilever, (b) relates to applying a negative pressure and picking up the microscopic object, (c) relates to a displacement in an x-y-plane, and (d) relates to the force-controlled landing at a desired position and release of the microscopic object by means of an overpressure pulse.

A complete sequence of spatial manipulating steps is shown in FIG. 4: In a first step, the cantilever 12 approaches the object 23 to be manipulated in the z-direction. During this step, the force exerted on the object 20 by the tip is monitored by means of a laser beam 18 (reflected light beam in FIG. 4(a)). When the object 23 adheres to the tip by means of a negative pressure within the microchannel 15 of the cantilever 12, the object 23 is lifted in z-direction to separate it from the surface (FIG. 4(b)). After lift-off the object can be moved in the x-y-plane by moving the cantilever 12 with the cantilever translating means of the AFM, accordingly (FIG. 4(c)). During this step the negative pressure in the microchannel 15 is maintained. Finally, the object 20 may be placed elsewhere by approaching the surface in z-direction and applying a positive pressure to the microchannel 15 (FIG. 4(d)). Again, the force exerted on the object 20 by the tip during this step is monitored by means of the reflected laser beam 18.

Figure 5:
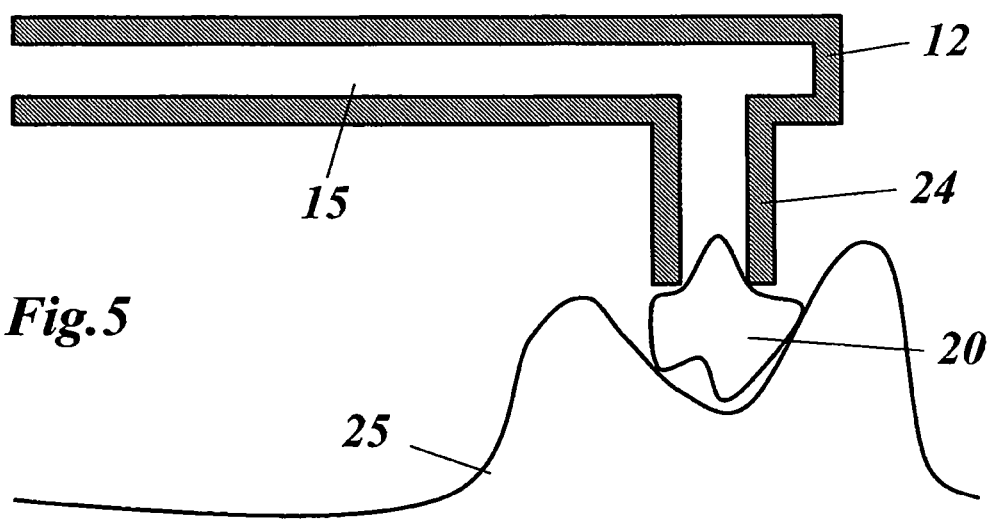
FIG. 5 shows the use of a cantilever with a high aspect ratio tip, e.g. in form of a hollow cylinder, to pick up a microscopic object embedded in a hollow of an uneven surface, according to an embodiment of the invention.

When the microscopic object 20 to be picked up is embedded in a hollow of an uneven surface 25 (FIG. 5), a cantilever 12 may be used, which comprises a high aspect ratio tip 24, e.g. in form of a hollow cylinder.

Figure 6:
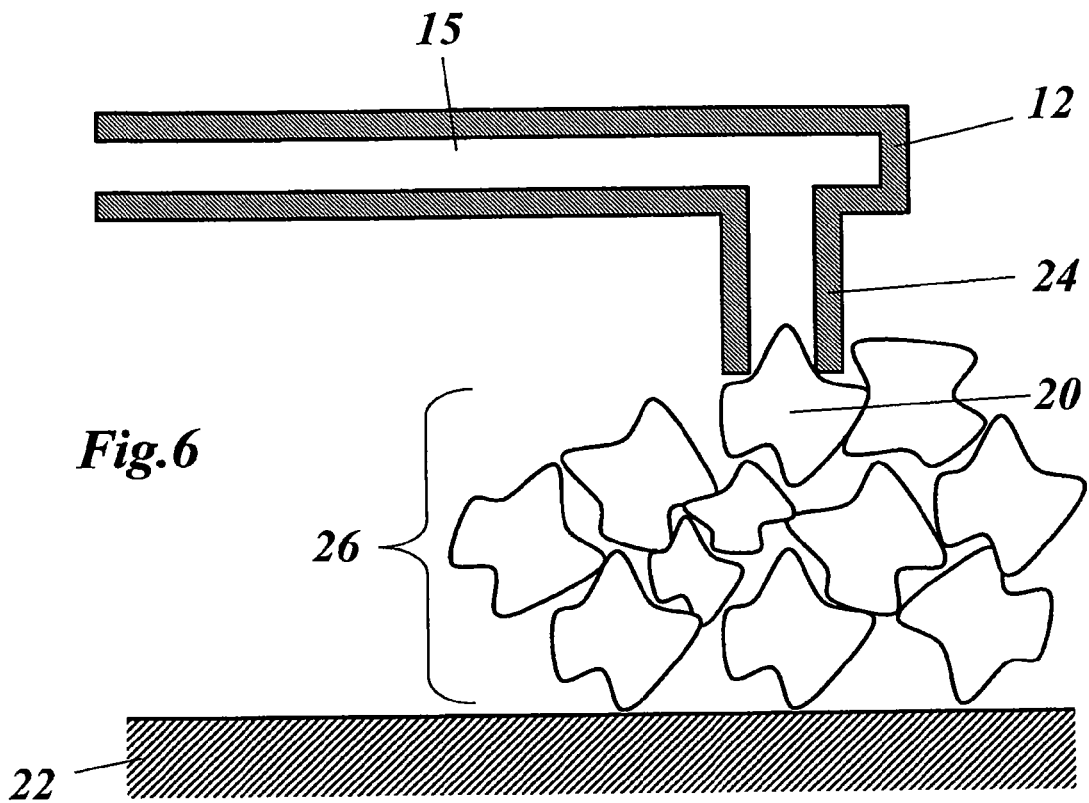
FIG. 6 shows the use of a cantilever with a high aspect ratio tip, e.g. in form of a hollow cylinder, to pick up a single microscopic object from inside an aggregation of objects, e.g. tissue, according to an embodiment of the invention.

Such tips are also able to pick up a single object from inside an object aggregation 26 (FIG. 6), e.g. tissue.

The microscopic objects 20 that can be spatially manipulated in the way described above can be living biological cells such as eukaryotic cells, yeast, bacteria or vesicles, viruses or solid material such as nanoparticles, crystals, fibers or polymeric material.

The same procedure can be applied to measure the adhesion force of any object to the surface by choosing the proper tip geometry, hole size and measuring the bending of the cantilever 12 when pulling the object away from the surface, e.g. an object-surface interaction or an object-object interaction. The same procedure can be used to remove parts of the object when the attachment force is stronger than the pulling force.

Figure 7:
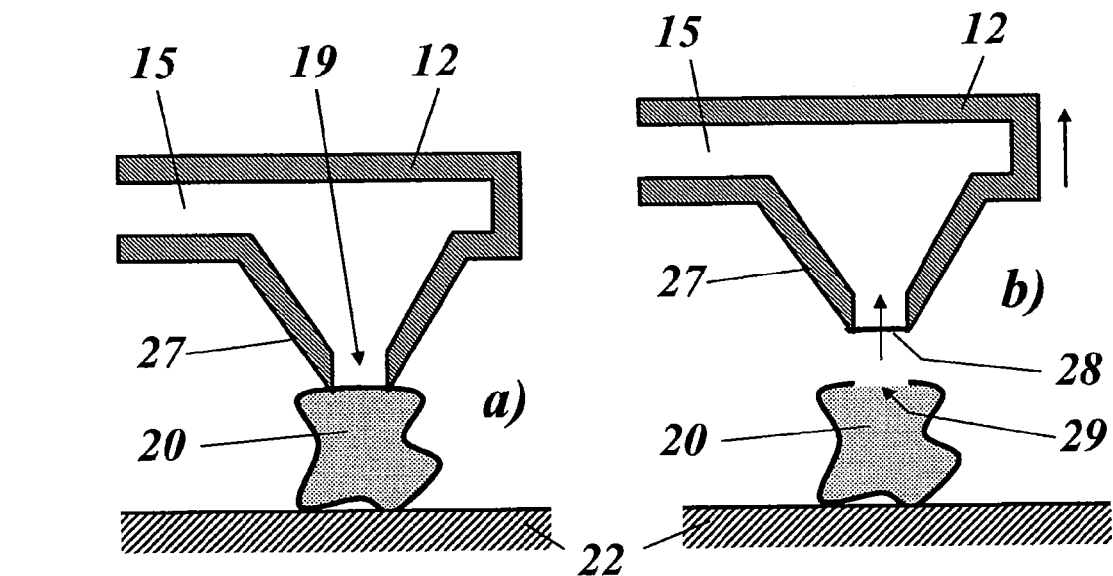
FIG. 7 shows the use of a cantilever with a sharpened tip to cut out a part of an object by applying negative pressure or pushing forces (a) and removing said part to either gain access to the inside of the object or use said part for further analysis (b), according to another embodiment of the invention.

When a cantilever 12 with a sharpened tip 27 is attached to the probeholder 11 (FIG. 7), the procedure can be used to cut into an object 20 using the sharp edges of the opening either by the force produced by the negative pressure or by pushing the cantilever 12 into the object 20 (FIG. 7(a)). The cutting 28 may be removed to either gain access to the inside of the object 20 through the cut-out 29, or to use said cutting 28 for further analysis (FIG. 7(b)).

Figure 8:
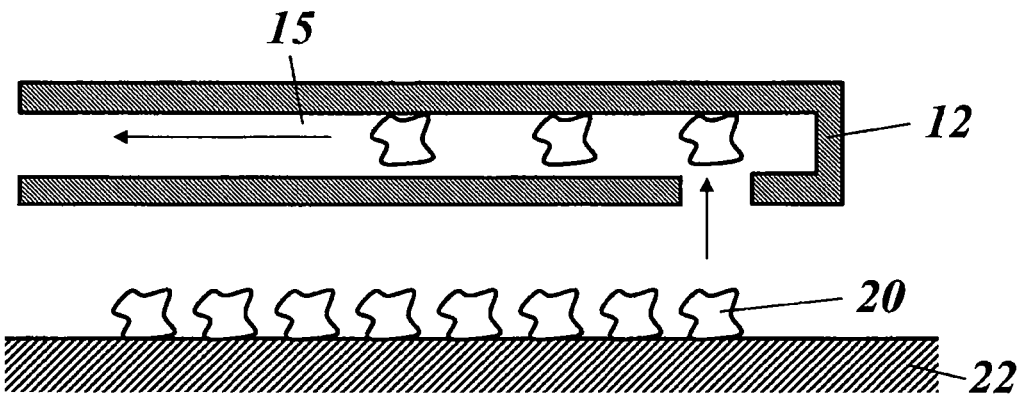
FIG. 8 shows the process of sucking microscopic objects into the microchannel of the cantilever, according to an embodiment of the invention.
Figure 9:
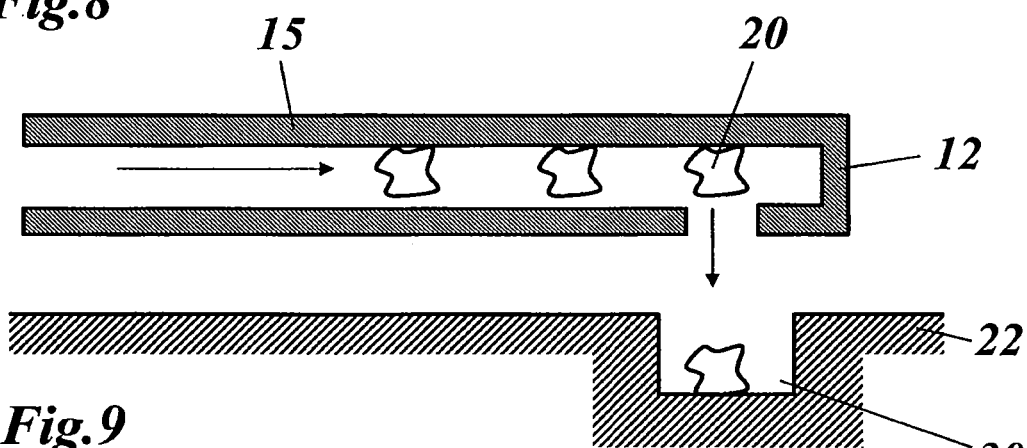
FIG. 9 shows the process of placing a microscopic object, which is released from the microchannel of the cantilever, into a recess, which may serve as a reacting tube, according to another embodiment of the invention.
Figure 10:
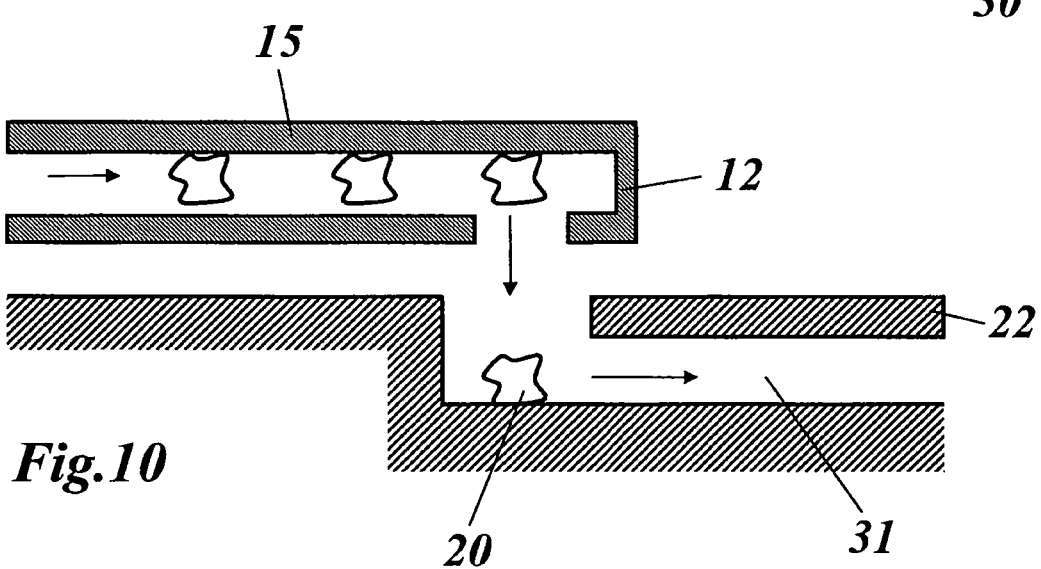
FIG. 10 shows the process of placing a microscopic object, which is released from the microchannel of the cantilever, into an opening, which may be part of an aspiration nozzle of an analytical device, according to another embodiment of the invention.

If the opening 19 (and the cross section of the microchannel 15) is larger than the object 20, one or more object(s) can be collected inside of the hollow cantilever 12 and be dispensed somewhere else (FIG. 8, FIG. 9 and FIG. 10). For example, the objects 20 can be displaced/dispensed on a surface 22 or into a recess or hole 30 (FIG. 9). Especially, the hole can be an aspiration hole or nozzle 31 connected to an analytical tool such as a mass spectrometer, PCR machine or UV/VIS IR spectrometer, or the hole can be a reaction tube for further analysis, e.g. PCR, ELISA (FIG. 10).

Figure 14:
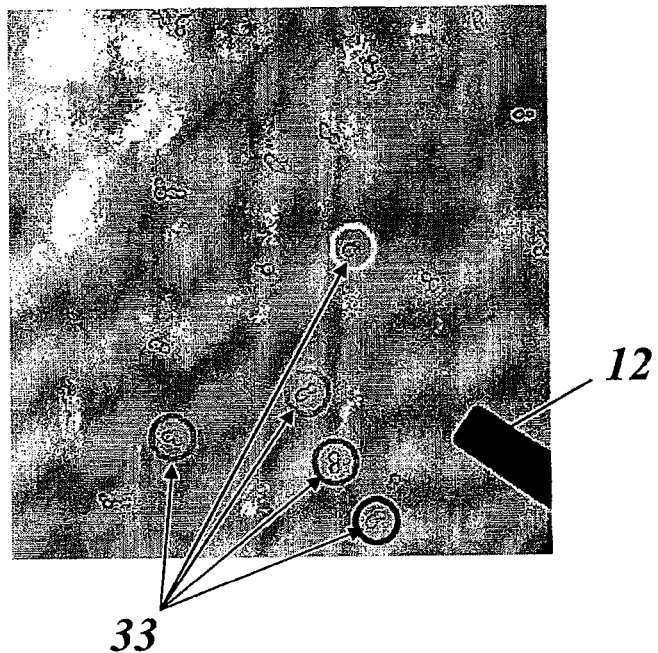
FIG. 14 shows a photograph of various yeast cells (circled) before being spatially manipulated.
Figure 15:
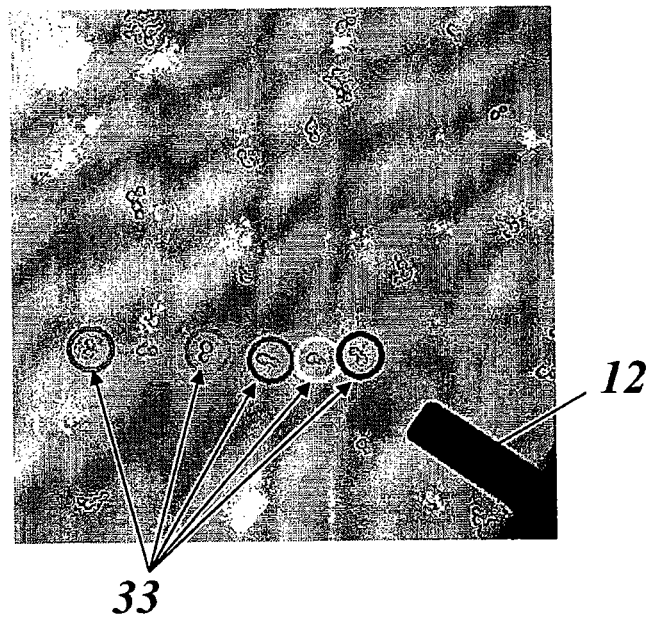
FIG. 15 shows the yeast cells of FIG. 14 after being aligned in a row by means of the method according to the invention.

FIGS. 14 and 15 show photographs (differential interference contrast images) of an exemplary spatial manipulation of single viable cells. FIG. 14 exhibits five yeast cells 33 (encircled) in an irregular configuration before the spatial manipulation with the cantilever 12. In FIG. 15, these five yeast cells 33 form a straight line after being manipulated in accordance with the present invention.

The "FluidFM" technology uses microchanneled AFM cantilevers which are fixed to an AFM probeholder. A continuous fluidic circuit is achieved connecting an external controlled pressure source with an aperture at the tip of the hollow cantilever. In this way, both an overpressure and an underpressure can be applied to the liquid inside the fluidic circuit. The invention combines a force-controlled approach with applied pressure to grasp living organisms cultured on a glass slide and displaces them with micrometric precision in a simple and reproducible way. In this way, myblasts, neurons, yeast and bacteria or other microscopic objects may be manipulated with high precision.

The invention claimed is:

1. A method for spatially manipulating a microscopic object (20, 23, 33), said method comprising the steps of:
providing an atomic force microscope (10) with a cantilever (12), said cantilever (12) fabricated by means of a micro-electro-mechanical systems technology, said cantilever (12) having a tip (13, 24, 27, 32) with a submicron opening (19) and a microchannel (15) extending through the cantilever (12) in its longitudinal direction, said microchannel (15) being fluidly connected to the opening (19) at the tip (13, 24, 27, 32) of the cantilever (12);
providing suspension means (11) for holding the cantilever (12) and spatially moving the cantilever (12) along a predetermined spatial path;
providing pressurizing means (14, 16, 17) for applying a predetermined pressure to the microchannel (15) within the cantilever; moving the cantilever (12) with its tip (13, 24, 27, 32) to the microscopic object (20, 23, 33) to be spatially manipulated, such that the opening (19) of the tip (13, 24, 27, 32) is adjacent to the microscopic object (20, 23, 33);
picking up, with said cantilever (12), at least a part (28) of the microscopic object (20, 23, 33) by reducing the pressure within the microchannel (15) relative to the pressure outside the tip (13, 24, 27, 32) of the cantilever (12), wherein a corresponding deflection (d) of the cantilever (12), which is due to an adhesion force (21) acting between said microscopic object (20, 23, 33) and a surface (22) supporting said microscopic object (20, 23, 33), is measured and said corresponding deflection (d) is used to calculate said adhesion force (21); and
moving said at least a part (28) of the microscopic object (20, 23, 33) along a predetermined spatial path by means of the cantilever (12).

2. The method according to claim 1, wherein, in a further step, said at least a part (28) of the microscopic object (20, 23, 33) is released from the cantilever (12) by increasing the pressure within the microchannel (15) relative to the pressure outside the tip (13, 24, 27, 32) of the cantilever (12).

3. The method according to claim 1, wherein said at least a part (28) of the microscopic object (20, 23, 33) is picked up by introducing it into the interior of the cantilever (12), especially into the microchannel (15) of the cantilever (12).

4. The method according to claim 2, wherein said at least a part (28) of the microscopic object (20, 23, 33) is released into a recess (30) or into an opening (31) of a processing means for being processed.

5. The method according to claim 1, wherein a cantilever (12) with an elongated tip (24) of high aspect ratio extending perpendicular to the longitudinal direction of the cantilever (12) is used to pick up at least a part of one specific microscopic object (20) from an aggregation (26) of several microscopic objects (20).

6. The method according to claim 1, wherein a cantilever (12) with a sharpened tip (27) extending perpendicular to the longitudinal direction of the cantilever (12) is used to tear off a part (28) of a microscopic object (20, 23, 33).

7. The method according to claim 1, wherein the pressurizing means (14, 16, 17) comprises a pressure source (17), which produces by means of a pump or by capillary, osmotic or electro-osmotic forces.

8. The method according to claim 1, wherein a cantilever (12) is used, the surface of which is modified to avoid an adhesion of the microscopic object (20, 23, 33), and especially by either having hydrophilic or hydrophobic properties.

9. The method according to claim 1, wherein, during picking up, the impedance through the opening (19) of the cantilever is measured in order to characterize the tightness of the microscopic object (20, 23, 33) closing the opening (19).

10. The method according to claim 1, wherein the impedance through the microchannel (15) of the cantilever is measured in order to determine the number and/or mass of microscopic objects (20, 23, 33) collected in said microchannel (15) after being picked up by said cantilever (12).

11. The method according to claim 1, wherein the cantilever (12) is sensed by means of a laser beam (18) in order to determine the number and/or mass of microscopic objects (20, 23, 33) collected in said microchannel (15) after being picked up by said cantilever (12).

12. A device for spatially manipulating a microscopic object (20, 23, 33) comprising:
an atomic force microscope (10) with a cantilever (12), said cantilever (12) fabricated by means of a micro-electro-mechanical-system technology, said cantilever (12) having a tip (13, 24, 27, 32) with an opening (19) and a microchannel (15) extending through the cantilever (12) in its longitudinal direction, said microchannel (15) being fluidly connected to the opening (19) at the tip (13, 24, 27, 32) of the cantilever (12);
suspension means (11) for holding the cantilever (12) and spatially moving the cantilever (12) along a predetermined spatial path; and
pressurizing means (14, 16, 17) for applying a predetermined pressure to the microchannel (15) within the cantilever; characterized in that said pressurizing means (14, 16, 17) is configured to generate a pressure within the microchannel (15) which is lower than the pressure outside the tip (13, 24, 27, 32) of the cantilever (12), and that an impedance measuring means (34, 35) is provided for measuring the hydraulic impedance within the cantilever (12), wherein the microchannel (15) of the cantilever (12) is configured to receive one or more of said microscopic objects (20, 23, 33) by the opening (19) and the cross section of the microchannel (15) being larger than one or more of said microscopic objects (20, 23, 33).

13. The device according to claim 12, wherein the cantilever (12) includes an elongated, especially cylindrical, tip (24) of high aspect ratio extending perpendicular to the longitudinal direction of the cantilever (12).

14. The device according to claim 12, wherein the cantilever (12) has a sharpened tip (27) extending perpendicular to the longitudinal direction of the cantilever (12).

15. The device according to claim 12, wherein the cantilever (12) includes a pyramidal tip (32) extending perpendicular to the longitudinal direction of the cantilever (12).

16. The device according to claim 12, wherein the opening (19) of the cantilever is flush with an outer surface of the cantilever (12).

17. A method for spatially manipulating a microscopic object (20, 23, 33), said method comprising the steps of:
providing an atomic force microscope (10) with a cantilever (12), said cantilever (12) fabricated by means of a micro-electro-mechanical systems technology, said cantilever (12) having a tip (13, 24, 27, 32) with an opening (19) and a microchannel (15) extending through the cantilever (12) in its longitudinal direction, said microchannel (15) being fluidly connected to the opening (19) at the tip (13, 24, 27, 32) of the cantilever (12);
providing suspension means (11) for holding the cantilever (12) and spatially moving the cantilever (12) along a predetermined spatial path;

providing pressurizing means (14, 16, 17) for applying a predetermined pressure to the microchannel (15) within the cantilever; moving the cantilever (12) with its tip (13, 24, 27, 32) to the microscopic object (20, 23, 33) to be spatially manipulated, such that the opening (19) of the tip (13, 24, 27, 32) is adjacent to the microscopic object (20, 23, 33);

picking up, with said cantilever (12), at least a part (28) of the microscopic object (20, 23, 33) by reducing the pressure within the microchannel (15) relative to the pressure outside the tip (13, 24, 27, 32) of the cantilever (12); and moving said at least a part (28) of the microscopic object (20, 23, 33) along a predetermined spatial path by means of the cantilever (12); and wherein, during picking up, a hydraulic impedance through the opening (19) of the cantilever is measured in order to characterize a tightness of the microscopic object (20, 23, 33) closing the opening (19).

\* \* \* \* \*